United States Patent [19]
Gaffar et al.

[11] Patent Number: 5,401,723
[45] Date of Patent: Mar. 28, 1995

[54] GLYCOCONJUGATE INHIBITION OF STREPTOCOCCUS PYROGENES ADHESION

[75] Inventors: Abdul Gaffar, Princeton, N.J.; Ronald Gibbons, Boston, Mass.; Stanislawa Tylewska, Warsaw, Poland

[73] Assignees: Colgate-Palmolive Company, Piscataway, N.J.; Forsyth Dental, Boston, Mass.

[21] Appl. No.: 984,441

[22] Filed: Dec. 2, 1992

[51] Int. Cl.$^6$ .................... A61K 37/02; A61K 47/36; A61K 31/70
[52] U.S. Cl. ........................... 514/21; 514/54; 536/55.1; 536/55.2; 536/55.3; 525/54.1; 424/49
[58] Field of Search ............ 514/21, 54; 536/55.1, 536/55.2, 55.3; 525/54.1; 424/49

[56] References Cited

U.S. PATENT DOCUMENTS

| | | | |
|---|---|---|---|
| 3,155,580 | 11/1964 | Bergy et al. | 167/65 |
| 4,357,326 | 11/1982 | Nair et al. | 424/180 |
| 4,376,761 | 3/1983 | Okami et al. | 424/48 |
| 4,457,921 | 7/1984 | Stroz et al. | 424/180 |
| 4,464,360 | 8/1984 | Leffler et al. | 424/180 |
| 4,587,119 | 5/1986 | Bucke et al. | 424/48 |
| 4,659,561 | 4/1987 | Fives-Taylor et al. | 424/48 |
| 4,661,345 | 4/1987 | Tuomanen | 424/85 |
| 4,859,656 | 8/1989 | Kjelleberg et al. | 514/54 |
| 4,891,210 | 4/1990 | Norris | 424/50 |
| 4,920,100 | 8/1991 | Lehmann et al. | 514/23 |
| 5,002,759 | 3/1991 | Gaffar et al. | 424/49 |
| 5,034,516 | 7/1991 | Roy et al. | 536/4.1 |
| 5,037,637 | 8/1991 | Gaffar et al. | 424/52 |
| 5,059,654 | 10/1991 | Hou et al. | 525/54.1 |
| 5,080,887 | 1/1992 | Gaffar et al. | 424/52 |
| 5,089,255 | 2/1992 | Gaffar et al. | 424/52 |
| 5,095,106 | 3/1992 | Gaffar et al. | 536/123 |
| 5,190,746 | 3/1993 | Cassels | 424/49 |

FOREIGN PATENT DOCUMENTS 0126043 11/1984 European Pat. Off. .
0209493 1/1987 European Pat. Off. .

OTHER PUBLICATIONS

Alberto et al., "Molecular Biology of The Cell", published by Garland Publishing, Inc., 1983, pp. 702 to 709.

*Primary Examiner*—Michael G. Witshyn
*Assistant Examiner*—C. Sayala
*Attorney, Agent, or Firm*—Robert C. Sullivan; Robert L. Stone

[57] ABSTRACT

Enhancement of the method and oral compositions for inhibiting adherence of *Streptococcus pyogenes* to pharyngeal and oral mucosa cells by treating these areas with a glycoconjugate comprising an oligosaccharide linked to a carrier. The oligosaccharide should have at least one fucose moiety or a galatose moiety which is free of digalactose and N-acetylneuraminyl lactose. The carrier may include albumins, starch or synthetic polymers.

13 Claims, No Drawings

GLYCOCONJUGATE INHIBITION OF STREPTOCOCCUS PYROGENES ADHESION

This invention was made with Government support under Grant Number DE-02847 awarded by the National Institutes of Health. The Government has certain rights in this invention.

FIELD OF THE INVENTION

This invention relates to an improved method of inhibiting adherence, and promoting desorption of, *Streptococcus pyogenes* to soft tissue surfaces, such as the pharyngeal and oral mucosa, by treating these areas with a conjugated oligosaccharide.

SUMMARY OF THE INVENTION

The object of this invention is to inhibit the attachment of *S. pyogenes* to human epitheliel cells by treating the cells with an oligosaccharide conjugated to a carrier.

Another object of the invention is to increase the retention time of these sugars at soft tissue surfaces. This provides a longer lasting effect for reducing the adhesion of *S. pyogenes* on such tissue surfaces as in the throat by preventing quick washing away of the oligosaccharides.

A further object of this invention is to prevent or treat sore throats by treating the pharyngeal and oral mucosa with conjugated oligosaccharides.

Conventional therapy for *S. pyogenes* infections has mainly consisted of treatment with antibiotics such as penicillin and tetracycline. Unfortunately, antibiotics such as penicillin and tetracycline exhibit broad spectrum antimicrobial activity. Thus, treatment with these antibiotics tends to kill not only *S. pyogenes* but a number of other bacterial species, some of which may actually be beneficial to the body. In contrast, the present invention by using conjugated oligosaccharides to specifically inhibit the adherence of *S. pyogenes* to pharyngeal and oral mucosal cells, does not disturb the normal microbial ecology of the mouth. Further, many oligosaccharides are derived from natural sources which are endogenous, and therefore unlikely to be, disruptive to the body.

BACKGROUND OF THE INVENTION

Adherence is an important early event in the pathogenesis of bacterial infections in animals and humans. Studies have shown that the infectious ability of bacteria is related to the ability of bacteria to adhere to host cells. In the first stages of infection, bacterial adhesins, adhesive molecules on the surface of bacteria, bind to receptor materials on the host cell membrane.

Surprisingly, it has been found that the adherence of the bacterium such as *Streptococcus pyogenes*, to human epithelial pharangeal and oral mucosal cells can be inhibited by oligosaccharides. *Streptococcus Pyogenes*, a group A beta hemolytic streptococci which cause pharyngitis, exhibits tissue tropism, i.e. it is virtually found only in humans.

In previous U.S. Pat. Nos. 5,002,759 and 5,095,106, which we herewith incorporate by reference, we described the oligosaccharide compositions and methods therewith that inhibit the adhesion of *S. pyogenes* on pharyngeal and oral mucosa. It has now been found that the inhibitory activity of these oligosaccharides can be substantially enhanced by coupling them with a carrier to make glycoconjugates.

DETAILED DESCRIPTION

The present invention relates to the inhibition of *S. pyogenes* adhesion to human pharyngeal and oral mucosal cells by conjugated oligosaccharides.

The oligosaccharide contains two or more, preferably 3 or more sugar residues, at least one of which is a galactose moiety free of digalactose and N-acetylneuraminyl lactose, or a fucosyl moiety. It presently appears that the exact linkage between the galactose moiety or fucose moiety and other sugar residues does not affect the utility of the oligosaccharides of the invention.

Preferred oligosaccharides include: B-trisaccharide, A-tetrasaccharide, 2-fucosyllactose, 3-fucosyllactose, lactose-N-tetrose, lactodifucotetraose, 3,'sialyllactose, etc.

The carriers, such as proteins, to be bonded to oligosaccharides may include various human animal blood proteins as well as synthetic proteins. They may include for example, animal serum albumins such as equine serum albumin, bovine serum albumin (BSA), rabbit serum albumin, human serum albumin, ovine serum albumin, albumen albumin and the like; animal serum globulins such as equine serum globulin, bovine serum globulin, rabbit serum globulin, human serum globulin, ovine serum globulin, alubmen globulin and the like; animal thyroglobulins such as equine thyroglobulin, bovine thyroglobulin, rabbit thyroglobulin, human thyroglobulin, ovine thyroglobulin and the like, animal hemoglobulin such as equine hemoglobulin, bovine hemoglobulin, rabbit hemoglobulin, human hemoglobulin, ovine hemoglobulin and the like, animal hemocyanins; edestin, polylysine, polyglutaminic acid, a lysineglutaminic acid copolymer, copolymer containing lysine or ornitine; etc.

Synthetic polymers, such as PVM/MA which is polyvinylmethyl ether/maleic acid polyacrylic acid, polymethacrylic acid, polyacrylamide, polystyrene or the like, which have functionalities for linking or may be funtionalized with amino groups, carboxyl groups, active olefins or the like. Further information as to the linking to polymers may be found in U.S. Pat. No. 5,059,654, which is herewith incorporated by reference.

Methods of linking the carrier and oligosaccharides are well known, for example by (A) isothiocyanate coupling (B) diazocoupling method, (C) amide bonding method, (D) reducing amination method, (E) introduction of sulfhydryl(thiol) groups etc. (Advances in Carbohydrate Chemistry and Biochemistry, Vol. 37 pp. 225–281 (1980); Methods in Enzymology, Vol. L. Complex Carbohydrates, Part C, pp. 155–175 (1978); Archives of Biochemistry and Biophsics, Vol. 205, No. 2, pp. 330–339 (1980).

According to the isothicyanate coupling method (A), thiophosgene is reacted with a compound obtained by a reducing amination reaction (wherein the saccharide is reacted, for example, with -(p-aminophenyl) ethylamine or like diamine derivative and $NaBH_4$, $NaBH_3CN$ or like reducing agent), and a carrier protein is coupled with the resulting isothiocyanate. The reducing amination reaction is carried out favorably in a suitable inert solvent, such as a buffer solution for example or 0.2 mole of calcium phosphate (pH=8), water, physiological saline or methanol, ethanol or like alcohol, at 0° to 40° C. for 3 hours to 3 days. Thiophosgene is reacted with a compound obtained by the amination reaction advantageously in a suitable inert solvent, such as water, 0.1 mole aqueous sodium hydrogencarbonate solutions (pH=8) or physiological saline, at −10° C. to room temperature for 30 minutes to 2 hours. Further the reaction between the isothiocyanate and the carrier protein is carried out favorably in a suitable inert solvent, such as water, physiological saline or 0.1 mole aqueous sodium hydrogencarbonate solution (pH=9.5), at −10° C. to room temperature for 15 to 20 hours.

The diazocoupling method (B) is practiced, for example, by reacting sodium nitrite and a diazotizing agent, such as hydrochloric acid or sulfuric acid, with the compound resulting from the reducing amination reaction of the method A to obtain a diazo compound, and coupling a carrier protein with the diazo compound. The diazotization reaction is conducted favorably in an inert-solvent, such as water, physiological saline or aqueous solution of hydrochloric acid or like mineral acid at −10° to −20° C. for 10 to 60 minutes. The carrier protein can be coupled with the diazo compound favorably at −10° to 20° C. in 2 to 6 hours.

The amine bonding method (C) is practiced, for example, by oxidizing the aldehyde group of the saccharide with silver oxide or like oxidizing agent to a sugar carboxylic acid, and subjecting the carboxyl group of the acid and the amino group of a carrier protein to an amide bonding reaction. The amide bonding reaction can be effected by the amide bond forming reaction of usual peptide, for example, by dehydration condensation reaction using a dehydrating agent such as 1-ethyl-3-(dimethylaminopropyl)-carbodiimide. This condensation reaction is carried out favorably in a suitable solvent such as 1 mole sodium acetate buffer solution (pH=5.5) or like buffer solution at 0° C. to room temperature for 3 to 12 hours.

The reducing amination method (D) is practiced, for example, by reacting the hapten with a carrier protein and a reducing agent such as $NABH_4$ or $HaBH_3CN$. This reaction can be carried out under the same conditions as the reducing amination reaction of the method A.

In the foregoing methods A to D, each reagent is used approximately in an equimolar amount, preferably an excessive amount, based on the material.

In this way, the desired (glycoconjugate) can be produced wherein an oligosaccharide is bonded to a carrier protein. The glycoconjugates resulting from the reaction can be easily isolated and purified, for example, by dialysis, gel filtration, fractionating precipitation or the like. Of the glycoconjugates thus produced, preferable are those which comprises 20 to 25 moles, on the average, of oligosaccharide per mole of the carrier protein as bonded thereto.

In method (E) the introduction of sulfhydryl groups into proteins, such as bovine serum albumin, is accomplished by treating the protein with a substituted anhydride such as S-acetylmercaptosuccinic anhydride (Klotz, Arch, Biochem, Biophys vol 96, pp. 605–612 (1962). The reaction takes place rapidly at room temperature under mild conditions, but the extent of thiolation is hardly affected by a change in temperature from 30° down to 0°. The pH may be in the 6.4–8 range, with the reaction run in a phosphate buffer (0.125M or 0.0625M). The concentration of protein to moles of reagent per $NH_2$ may be about 2 to 1. A specific oligosaccharide is reacted with the thiolated albumin to form a conjugate with the sulfhydryl group.

The procedure for testing the effects of oligosaccharide conjugates (see the Table) on the adhesion of *S. pyogenes* to human epithelial pharyngeal and oral mucosal cells is the same as that set forth in U.S. Pat. Nos. 5,002,759 or 5,095,106 in determining the effect of oligosaccharides.

Various oligosaccharide conjugates were added to the *S. pyogenes* epithelial cell mixture comprising cells from the pharangeal buccal or tongue surfaces. The measured decrease in relative absorption of *S. pyogenes* in the presence of the conjugates is shown in the following table.

ADHESION OF M POSITIVE *STREPTOCOCUS PYOGENES* STRAIN D47 TO HUMAN PHARYNGEAL CELLS IN THE PRESENCE OF GLYCOCONJUGATES

| Treatment | Conc. | Relative Adsorption % ± S.D. |
|---|---|---|
| Saline | — | 25.38 + 2.71 100% |
| Human Serum Albumin (HSA) | 1% | 27.15 + 2.15 |
| | 0.5% | 26.07 + 2.60 |
| Bovine Serum Albumin (BSA) | 1% | 27.95 + 1.06 |
| | 0.1% | 25.36 + 2.71 |
| Galactose (GAL) | 1 mg/ml | 14.83 + 2.72 |
| | 0.05% | 19.48 + 1.19 |
| Glucose | 1 mg/ml | 26.29 + 2.09 |
| 7-Antigen-HSA (Gal 1-3 Gal NAC) | 0.05 mg/ml | 11.6 + 0.64 45.9% |
| Lacto-N-Neotetaose-HSA | 0.05 mg/ml | 13.08 + 2.49 51.5% |
| Lacto-N-Tetraose-HSA | 0.05 mg/ml | 10.50 + 2.90 41.4% |
| Gangliotetraose-HSA | 0.05 mg/ml | 9.0 + 1.54 35.5 |
| Galbeta 1-4 GLC NAC beta 1-0-PAP-HSA (PAP in para-amino phenyl) | 0.05 mg/ml | 8.40 + 0.20 21.3 |
| LNF111-HSA* | 0.05% | 5.40 + 0.21 21.3 |

*Gal B1-4 Galc NAG B 1-3 Gal B 1-4 Galc 3,1, FUC 1

These results show that the adherence of *S. pyogenes* to epithelial pharangeal, buccal, or tongue mucosal surfaces is significantly inhibited by the glycoconjugates.

Preparations containing the glycoconjugates for oral application may be in any convenient orally acceptable form, such as a mouthrinse, tablet or lozenge, chewing gum, throat spray toothpaste or gel and the like. The oral application may also be in the form of elixirs, syrups or suspension, for example, solutions containing 0.1 to 5% by weight of a glycoconjugate and a mixture of ethanol, water glycerol, propylene glycol and optionally aroma, saccharine and/or sodium carboxymethylcellulose as a dispersing agent.

A mouthrinse or mouthwash may be prepared by mixing a nontoxic alcohol and water vehicle with flavoring oil, humectant, sweetener, color and optionally antibacterial antiplaque agent, for example, cetyl pyridinium chloride, benzethonium chloride, and chlorhexidine.

The mouthwash may also contain 0.5 to 5% of a water-soluble organic surfactant, typically an amphoteric surfactant such as, betaine, and most preferably a nonionic surfactant. Surfactant combinations such as that of an aminobetaine and a polyoxyethyleneated polyoxypropylene nonionic block polymer (Pluronic F-108; Pluronic F-127) are particularly effective in mouthrinses or washes.

The alcohol component of a mouthwash, typically present in an amount of about 5–25% by weight is a nontoxic alcohol such as isopropanol or ethanol, preferably utilizing denaturing components which also function as flavoring agents. These flavoring agents are used in an amount between about 1% and 2% of the total alcohol content of the mouthwash. Water typically comprises at least about 50% by weight of a mouthrinse and humectant about 5–40% by weight. Generally, the ratio of water to alcohol is in the range of from about 1:1 to about 20:1 preferably from 3:1 to 20:1 and most preferably from about 5:1 to 10:1 by weight. The total amount of water-alcohol mixture in this type of preparation is typically in the range of from bout 70 to about 99.9% by weight of the preparation.

EXAMPLE 1

| Mouthrinse | Percent |
|---|---|
| Alcohol | 5% |
| Glycerine | 10% |
| Flavor | 0.4% |
| Saccharine | 0.03% |
| Glycoconjugate (3'-Sialyllactose-HSA) | 0.1 to 5.0% |
| Triclosan | 0.03% |
| SLL | 0.15% |

The oligosaccharides conjugates of this invention can also be incorporated in lozenges or in chewing gum or other products, e.g. by stirring into a warm gum base or coating the outer surface of a gum base; illustrative of which may be mentioned jelutone, rubber latex, vinylite resins, etc., desirably with conventional filler materials such as plasticizers or softeners, sugar or other sweeteners or carbohydrates such as glucose, sorbitol, sorbitol syrup, mannitol, xylitol, hydrogenated starch hydrolysate, and the like, and artificial sweeteners for example, aspartame and L-aspartic acid derived sweeteners, saccharine salts, acesulfame-K and the like, and the free acid form of saccharine, and protein based sweeteners such as thaumatin.

A typical chewing gum may contain the following ingredients, in percent by weight based on the weight of the total gum formulation:

EXAMPLE 2

| Chewing Gum | Parts by Weight |
|---|---|
| Base Gum | 30.0% |
| Sorbitol | 42.5% |
| Mannitol | 4.0% |
| 70% Sorbitol in water | 16.5% |
| Glycerine | 5.0% |
| Glycoconjugate | 0.25% |
| Flavor Q.S. | 100% |

In certain sugarless gums, there is used as the binder ingredient a solution of sorbitol in water containing from about 10% to about 80%, preferably from about 50% to 75% by weight of sorbitol in H$_2$O. In others, there is used a gum acacia-in-water system containing from about 30% to about 60%, preferably from about 45% to about 50% by weight of gum acacia powder.

The ingredient referred to heretofore in the formulations simply as "gum base" is susceptible to many variations. In general, a gum base is prepared by heating and blending various ingredients, such as natural gums, synthetic resins, waxes, plasticizers etc. in a manner well known in the art. Typical examples of the ingredients found in a chewing gum base are masticatory substances of vegetable origin, such as chicle, crown gum, nispero, rosidinha, jelutong, pendare, perillo, niger gutta, tunu, etc., masticatory substances of synthetic origin such as butadiene-styrene polymer, isobutyleneisoprene copolymer, paraffin, petroleum wax, polyethylene, polyisobutylene, polyvinylacetate, etc.

A variety of traditional ingredients may be incorporated in the gum base, such as plasticizers of softeners. Examples of these ingredients include lanolin, stearic acid, sodium stearate, potassium stearate, glyceryl triacetate, glycerine, lecithin, glyceryl monostearate and the like. Natural waxes, petroleum waxes, polyurethane waxes, paraffin waxes and microcrystalline waxes may also be incorporated into the gum base to obtain a variety of desirable textures and consistency properties. Mixtures of these traditional ingredients are also contemplated. These traditional ingredients are generally employed in amounts of up to about 30% by weight, and preferably, in amounts of from about 3% to about 20% by weight of the final chewing gum product.

Mineral fillers may include aluminum hydroxide, alumina, aluminum silicate, titanium dioxide, talc, calcium carbonate, tricalcium phosphate, and mixtures thereof.

The flavoring which can be included in any of the compositions made according to this invention can include one or more natural and/or synthetic flavors and/or oils derived from plants, leaves, flowers and fruit. Representative flavors and oils of these types include acids such as adipic, succinic and fumaric acid; citrus oils such as lemon oil, orange oil, lime oil and grapefruit oil; fruit essences, such as apple essence, pear essence, peach essence, strawberry essence, apricot essence, raspberry essence, cherry essence, plum essence and pineapple essence; essential oils such as peppermint oil, spearmint oil, bay oil, anise oil, oil of nutmeg, oil of sage, oil of bitter almonds, cassia oil and methylsalicylate (oil of wintergreen). Various synthetic flavors, such as those for a mixed fruit, may also be incorporated in the chewing gum with or without conventional preservatives.

The vehicles or carrier in a tablet, lozenge or tooth paste is a noncariogenic water soluble polyhydric alcohol (polyol) such as mannitol, xylitol, sorbitol, maltitol, a hydrogenated starch hydrolysate for example Lycasin hydrogenated disaccharides and hydrogenated polysaccharides, in an amount of about 90–98% by weight of the total composition. Solid salts such as sodium bicarbonate, sodium chloride, potassium bicarbonate or potassium chloride may totally or partially replace the polyol-carrier.

Tableting lubricants, in minor amounts of about 0.1 to 5% by weight, may be incorporated into the tablet or lozenge formulation to facilitate the preparation of both the tablets and lozenges. Suitable lubricants include vegetable oils such as coconut oil, magnesium stearate, aluminum stearate, talc, starch and Carbowax.

Lozenge formulations may contain about 2% gum as barrier agent to provide a shiny surface as opposed to a tablet which has a smooth finish, suitable non-cariogenic gums include polycarboxylates such as Kappa carrageenan, carboxymethyl cellulose, hydroxyethyl cellulose, Gantrez and the like.

The lozenge or table may optionally be coated with a coating material such as wax, shellac, sodium carboxymethyl cellulose, polyethylene/maleic anhydride copolymer or kappacarrageenan to further increase the time it takes the tablet or lozenge to dissolve in the mouth. The uncoated tablet or lozenge is slow dissolving, providing a sustained release rate of active ingredients of about 3 to 5 minutes. Accordingly, the solid dose tablet and lozenge composition of this invention affords a relatively longer time period of contact with active ingredients.

Examples of lozenge formulations which may be employed in the method of the present invention are as follows:

Example 3

| Lozenge | Weight % |
| --- | --- |
| Sorbitol | 97.2 |
| Corn Syrup | 2 |
| Flavor Oil | 0.5 |
| Magnesium Stearate | 0.15 |
| Glycoconjugate | 0.1 |
| Water | 0.05 |

One or more organic surface-active agents are used in the compositions of the present invention to achieve increased wetting, foaming and prophylactic action, assist in achieving thorough and complete dispersion of the composition throughout the oral cavity, and render the instant compositions more cosmetically acceptable. The organic surface-active material is preferably anionic, nonionic or ampholytic in nature, and it is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkyl sulfoacetates, higher fatty acid esters of 1,2-dihydroxy propane sulfonate, and the substantially saturated higher aliphatic acyl amides of lower aliphatic amino carboxylic acid compounds such as those having 12 to 16 carbons in the fatty acid, alkyl or acyl radicals, and the like. Examples of the last mentioned amides are N-lauroyl sarcosin and the sodium potassium, and ethanolamine salts of N-lauroyl, N-myristoyl, or N-palmitoyl sarcosine which should be substantially free from soap or similar higher fatty acid material. The use of these sarcosinate compounds in the oral compositions of the present invention is particularly advantageous since these materials exhibit a prolonged and marked effect in the inhibition of acid formation in the oral cavity due to carbohydrate breakdown in addition to exerting some reduction in the solubility of tooth enamel in acid solutions.

Examples of water-soluble nonionic surfactants are condensation products of ethylene oxide and various reactive hydrogen-containing compounds reactive therewith having long hydrophobic chains (e.g. aliphatic chains of about 12 to 20 carbon atoms), which condensation products ("ethoxamer") contain hydrophilic polyoxyethylene moieties, such as condensation products of poly(ethylene oxide) with fatty acids, fatty alcohols, fatty amides, polyhydric alcohols (e.g. sorbitan monostearate) and polypropyleneoxide (e.g. Pluronic materials).

Various other materials may be incorporated in the oral preparations of this invention particularly the tooth paste (cream) or gels, such as whitening agents, preservatives, silicones, chlorophyll compounds, other anticalculus agents, and/or ammoniated material such as urea, diammonium phosphate, organic or inorganic fluorides, etc.

The toothpaste (cream) or dental gel typically contains an orally or dentally acceptable polishing agent for use in conjunction with brushing of the teeth. Examples of such agents and formulations of desirable dental and oral treating means are set forth in U.S. Pat. Nos. 5,089,255 and 5,080,887, which are herewith incorporated by reference.

The polishing material is generally present in the solid or pasty compositions in weight concentrations of about 10% to about 99%. Preferably, it is present in amounts ranging from about 10% to about 75% in toothpaste or gel and from about 70% to about 99% in toothpowder or tablet.

In a toothpaste, dental cream or gel, the liquid vehicle is typically water in concentrations of about 2% to about 50% and mixed with about 0.2 to about 5 parts of humectant per part by weight of the water. The active xylitol may function as part or all of the humectant, Glycerine, propylene glycol, sorbitol, polypropylene glycol and/or polyethylene glycol (e.g. 400–600) exemplify suitable humectants/carriers. Also advantageous are liquid mixtures of water, glycerine and sorbitol. In clear gels where the refractive index is an important consideration about 3–30 wt. % of water, 0 to about 80 wt % of glycerine, and about 20–80 wt. % of sorbitol is preferably employed.

Toothpastes (creams) and gels typically contain a natural or synthetic binder, thickener or gelling agent in proportions of about 0.1 to about 10, preferably about 0.5 to about 5, wt %. A suitable thickener is synthetic hectorite, a synthetic colloidial magnesium alkali metal silicate complex clay available for example as Laponite (e.g. CP, SP 2002, D) marketed by Laporte Industries Limited. Laponite D analysis shows, approximately by weight 58.00% $SiO_2$ 25.40% MgO, 3.05% $Na_2O$, 0.98% $Li_2O$ and some water and trace metals. Its true specific gravity is 2.53 and it has an apparent bulk density (g/ml at 8% moisture) of 1.0.

Other suitable thickeners include Irish moss, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose and colloidal silica such as finally ground Syloid (e.g. 244)

Example 4

| Toothpaste | Percent |
| --- | --- |
| Glycerine | 13 |
| Sorbitol | 6 |
| SLS | 1.5 |
| CMS | 1.5 |
| Saccharin | 0.3 |
| $SiO_2$ | 12 |
| Glycoconjugate | 2 |
| Flavor | 0.95 |
| Triclosan | 0.3% |
| Water Q.S | 100% |

The glycoconjugates can be incorporated in many additional formations as will be obvious to those skilled in the art and may be utilized by conventional means in the treatment of soft tissue surfaces to inhibit *S. pyogenes* adhesion thereto.

We claim:

1. A method of inhibiting adherence of *Streptococcus pyogenes* to epithelial pharyngeal and oral cells comprising contacting said cells in the oral cavity with an oligosaccharide which is conjugated to a protein, a synthetic polymer or starch.

2. A method of preventing or treating a sore throat caused by *Streptococcus pyogenes* comprising applying to the soft mucosal surface of the throat an oligosaccharide which is conjugated to a protein, a synthetic polymer or starch which inhibits the adherence of said bacteria to said surface.

3. A method of inhibiting the adherence of *Streptococcus pyogenes* to the oral or pharyngeal mucosa comprising applying a oligosacchride which is conjugated to a protein, a synthetic polymer or starch thereto.

4. The method of claims 1, 2 or 3 wherein the oligosaccharide contains at least one fucose moiety or a galactose moiety which is free of N-acetylneuraminyl lactose.

5. The method of claims 1, 2 or 3 wherein the protein is an albumin.

6. The method of claims 1, 2 or 3 wherein the oligosaccharide is selected from the group consisting of A-tetrasaccharide, B'-sialyllactose, lacto-N-tetraose, B-trisaccharide, fucosyllactose, lacto-N-neotetraose and gangliotetraose, and the oligosaccharide is conjugated to human serum albumin or bovine serum albumin.

7. The method of claims 1, 2 or 3 wherein the oligasaccharide—conjugate is Gal 1-3 Gal N-acetyl-Human Serum Albumin, lacto-N-fucopentaose 1,1,1—Human Serum Albumin, Galbeta 1-4 galactose N-acetyl beta 1-0-para amino phenyl Human Serum Albumin.

8. An oral composition comprising an orally acceptable vehicle and an oligosaccharide which is conjugated to a protein, a synthetic polymer or starch, the oligosaccharide-conjugate being in an amount to effectively inhibit the adherence of *Streptococcus pyogenes* to oral or pharyngeal mucosa or the cells thereof.

9. The oral composition of claim 6 wherein the orally acceptable vehicle comprises a mouthrinse, mouthwash, toothpaste, chewing gum or lozenge.

10. The composition of claim 8 wherein the oiigosaccharide contains at least one fucose moiety or a galactose moiety which is free of N-acetylneuraminyl lactose.

11. The composition of claim 6 wherein the oligosaccharide is selected from the group consisting of A-tetrasaccharide, B'-sialyllactose, lacto-N-tetraose, B-trisaccharide, fucosyllactose, lacto-N-neotetraose and gangliotetraose, and the oligosaccharide is conjugated to human serum albumin or bovine serum albumin.

12. The composition of claim 8 wherein the oligosaccharide—conjugate is Gal 1-3 Gal N-acetyl-Human Serum Albumin, lacto-N-fucopentaose 1,1,1-Human Serum Albumin, Galbeta 1-4, galactose N-acetyl beta 1-0-para amino phenyl Human Serum Albumin.

13. The composition of claim 8 wherein the synthetic polymer is polyacrylic acid, polymethacrylic acid, polyvinylmethyl ether/maleic acid, polyacrylamide or polystyrene.

* * * * *